United States Patent [19]

Burlingame

[11] Patent Number: 5,856,148
[45] Date of Patent: *Jan. 5, 1999

[54] MATERIALS AND METHODS FOR BIOSYNTHESIS OF SERINE AND SERINE-RELATED PRODUCTS

[75] Inventor: Richard P. Burlingame, Manitowoc, Wis.

[73] Assignee: Wacker Chemie GmbH, München, Germany

[ * ] Notice: The term of this patent shall not extend beyond the expiration date of Pat. No. 5,618,716.

[21] Appl. No.: 797,727

[22] Filed: Feb. 11, 1997

Related U.S. Application Data

[63] Continuation-in-part of Ser. No. 244,491, filed as PCT/EP92/01873, Aug. 17, 1992.

[30] Foreign Application Priority Data

Dec. 12, 1991 [EP] European Pat. Off. ............. 91121385

[51] Int. Cl.$^6$ .............................. C12N 9/04; C12N 15/53
[52] U.S. Cl. ......................... 435/106; 435/108; 435/190; 435/325; 435/419; 435/252.3; 435/252.33; 536/23.2; 935/10; 935/14
[58] Field of Search ..................................... 435/106, 108, 435/190, 325, 419, 252.3, 252.33; 536/23.2; 935/10, 14

[56] References Cited

U.S. PATENT DOCUMENTS

| | | | |
|---|---|---|---|
| 4,743,546 | 5/1988 | Backman et al. | 435/108 |
| 4,753,883 | 6/1988 | Backman et al. | 435/108 |

FOREIGN PATENT DOCUMENTS

| | | |
|---|---|---|
| 0190921 | 8/1986 | European Pat. Off. . |
| 0401735 | 12/1990 | European Pat. Off. . |
| 0418840 | 3/1991 | European Pat. Off. . |
| 0372962 | 7/1994 | European Pat. Off. . |

OTHER PUBLICATIONS

The Journal of Biological Chemistry, 1986 by the American Society of Biological Chemists, Inc., vol. 261, No. 26, pp. 12179–12183, Karen L. Tobey and Gregory A. Grant "The Nucleotide Sequence of the serA Gene of *Escherichia coli* and the Amino Acid Sequence of the Encoded Protein, D–3–Phosphoglycerate Dehydrogenase".

The Journal of Biological Chemistry, vol. 252, No. 8, pp. 1527–1551, 1977, Robert Dubrow and Lewis I. Pizer, "Transient Kinetic Studies on the Allosteric Transition of Phosphoglycerate Dehydrogenase".

Journal of Bacteriology, Jan. 1980, pp. 235–245, vol. 141, No. 1, John C. McKitrick and Lewis I. Pizer "Regulation of Phosphoglycerate Dehydrogenase Levels and Effect on Serine Synthesis in *Escherichia coli* K–12".

Journal of Bacteriology, Jun. 1971, pp. 972–982, vol. 106, No. 3, Tetsuya Tosa and Lewis I. Pizer, "Biochemical Bases for the Antimetabolite Action of L–Serine Hydroxamate".

T. M. Roberts et al., Gene 12 (1980), 123–127, Elsevier/North–Holland Biomedical Press "A plasmid cloning vehicle allowing a positive selection for inserted fragments".

Experiments in Molecular Genetics, Cold Spring Harbor Press, pp. 201–205, Miller (1972), "Generalized Transduction; Use of P1 in Strain Construction".

Amundsen et al. (1986), Proc. Acad. Sci., U.S.A. 82, pp. 5558–5562, vol. 83 "The gene for an essential third subunit of exonuclease V".

Shevell et al. (1988), J. Bacteriol. 170, p. 3294–3296, vol. 170, No. 7 "Construction of an *Escherichia coli* K–12 ada Deletion by Gene Replacement in a recD Strain Reveals a Second Methyltransferase That Repairs Alkylated DNA".

Experiments in Mol. Genetics, Cold Spring Harbor Lab., pp. 201–205 (1972), "Generalized Transduction; Use of P1 in Strain Construction".

Crueger and Crueger (1982) (Biotechnology: A Textbook of Industrial Microbiology) Herrmann and Somerville (1983) (Amino Acids: Biosynthesis and Genetic Regulation) are well–known textbooks which teach standard biochemical procedures.

Journal of Biological Chemistry, vol. 264, No. 5, 15 Feb. 1989, pp. 2654–2648, Baltimore, US, D.J. Schuller et al.: "Enhanced expression of the *Escherichia coli* serA gene in plasmid vector. Purification, crystallization, and preliminary X–ray data of D–3 phosphoglycerate dehydrogenase".

Bioscience Reports, vol. 1, No. 9, 1981, pp. 733–741, London, GB, G.A. Grant et al.: "D–3–phosphoglycerate dehydrogenase from *Escherichia coli*: Isolation by affinity chromatography and sequence comparison to other dehydrogenases".

Journal of Bacteriology, vol. 173, No. 5, Mar. 1991, p. 1571, Baltimore, US, K. O'Day et al.: "Physical location of bg1A and serA on the *Escherichia coli* K–12 chromosome".

Journal of Molecular Biology, vol. 186, No. 4, 20 Dec. 1985, pp. 707–713, London, GB, R. Cunin et al.: "Structure–function relationship in allosteric aspartate carbamoyltransferase from *Escherichia coli*. I. Primary structure of a pyrI gene encoding a modified regulatory subunit".

*Primary Examiner*—Keith D. Hendricks
*Attorney, Agent, or Firm*—Collard & Roe, P.C.

[57] ABSTRACT

Engineered DNA encoding 3-phosphoglycerate dehydrogenase (PGD) has reduced sensitivity to inhibition by serine in comparison to wild-type PGD. The DNA encodes PGD which has at least some level of enzymatic activity useful for biosynthesis, and which retains that activity at higher serine levels than does the (unmodified) wild-type PGD. The PGD has the amino acid sequence of this above-described engineered DNA. Expression vectors contain this engineered DNA and regulatory DNA positioned and oriented for expression of the engineered DNA in a host expression system. Cells contain these expression vectors, and a method for producing serine or a serine-derived product includes culturing such cells.

11 Claims, 7 Drawing Sheets

FIG. 2-1

ATGGCAAAGGTATCGCTGGAGAAGACAAGATTAAGTTTCTGCTGGTAGAAGGCGTGCAC
MetAlaLysValSerLeuGluLysAspLysIleLysPheLeuLeuValGluGlyValHis

CAAAAGGCGCTGGAAAGCCTTCGTGCAGCTGGTTACACCAACATCGAATTTCACAAAGGC
GlnLysAlaLeuGluSerLeuArgAlaAlaGlyTyrThrAsnIleGluPheHisLysGly

GCGCTGGATGATGAACAATTAAAAGAATCCATCCCCGATGCCCACTTCATCGGCCTGCGA
AlaLeuAspAspGluGlnLeuLysGluSerIleArgAspAlaHisPheIleGlyLeuArg

TCCCGTACCCATCTGACTGAAGACGTGATCAACGCCCGAGAAAAACTGGTCGCTATTGGC
SerArgThrHisLeuThrGluAspValIleAsnAlaAlaGluLysLeuValAlaIleGly

TGTTTCTGTATCGGAACAAACCAGGTTGATCTGGATGCGGGGCAAAGCGCGGGATCCCG
CysPheCysIleGlyThrAsnGlnValAspLeuAspAlaAlaLysArgGlyIleProPro

FIG. 2-2

```
310                                                          350
GTATTTAACGCACCGTTCTCAAATACGCGCTCTCTGTTGCGGAGCTGGTGATTGGCGAACTG
ValPheAsnAlaProPheSerAsnThrArgSerValAlaGluLeuValIleGlyGluLeu
                        330

370                                                          410
CTGCTGCTATTGCGCGGGCGTGCCGGAAGCCAATGCTAAAGCTGCCGGAAGCCAATGCTAAAGCC
LeuLeuLeuArgGlyValProGluAlaAsnAlaLysAlaAlaHisArgValTrpAsn
                        390

430                                                          470
AAACTGGCGGGCGGGTTCTTTTGAAGCGCGGCAAAAAGCTGGGTATCATCGGCTACGGT
LysLeuAlaAlaGlySerPheGluAlaArgGlyLysLysLeuGlyIleIleGlyTyrGly
                        450

490                                                          530
CATATTGGTACGCAATTGGGCATTCTGGCTGAATCGCTGGGAATGTATGTTTACTTTTAT
HisIleGlyThrGlnLeuGlyIleLeuAlaGluSerLeuGlyMetTyrValTyrPheTyr
                        510

550                                                          590
GATATTGAAAATAAACTGCCGCTGGGCAACGCCACTCAGGTACAGCATCTTTCTGACCTG
AspIleGluAsnLysLeuProLeuGlyAsnAlaThrGlnValGlnHisLeuSerAspLeu
                        570
```

FIG. 2-3

```
                    610                          630                          650
CTGAATATGAGCGGATGTGGTGAGTCTGCATGTACCAGAGAATCCGTCCACCAAAAATATG
LeuAsnMetSerAspValValSerLeuHisValProGluAsnProSerThrLysAsnMet 670                          690                          710
ATGGGCGCGAAAGAAATTTCACTAATGAAGCCCGGCTCGCTGATTAATGCTTCGCGC
MetGlyAlaLysGluIleSerLeuMetLysProGlySerLeuLeuIleAsnAlaSerArg 730                          750                          770
GGTACTGTGGTGGATATTCCGGCGCTGTGTGATGCGCTGGCGAGCAAACATCTGGCGGGG
GlyThrValValAspIleProAlaLeuCysAspAlaLeuAlaSerLysHisLeuAlaGly 790                          810                          830
GCGGCAATCGACGTATTCCCGACGGGAACCGGGCGACCAATAGCGATCCATTTACCTCTCCG
AlaAlaIleAspValPheProThrGluProAlaThrAsnSerAspProPheThrSerPro 850                          870                          890
CTGTGTGAATTCGACAACGTCCTTCTGACGCCACACATTGGCGGTTCGACTCAGGAAGCG
LeuCysGluPheAspAsnValLeuLeuThrProHisIleGlyGlySerThrGlnGluAla
```

FIG. 2-4

910                                  930                                     950
CAGGAGAATATCGGCCTGGAAGTTGCGGTAAAATTGATCAAGTATTCTGACAATGGCTCA
GlnGluAsnIleGlyLeuGluValAlaGlyLysLeuIleLysTyrSerAspAsnGlySer 970                                  990                                    1010
ACGCTCTCTGCGGTGAACTTCCCGGAAGTCTCGCTGCCACTGCACGGTGGGCGTCGTCTG
ThrLeuSerAlaValAsnPheProGluValSerLeuProLeuHisGlyGlyArgArgLeu 1030                                 1050                                   1070
ATGCACATCCACGAAAACCGTCCGGGCGTGCTAACTGCGCTGAACAAAATCTTCGCCGAG
MetHisIleHisGluAsnArgProGlyValLeuThrAlaLeuAsnLysIlePheAlaGlu 1090                                 1110                                   1130
CAGGGCGTCAACATCGCCGCGCAATATCTGCAAACTTCCGCCCAGATGGGTTATGTGGTT
GlnGlyValAsnIleAlaAlaGlnTyrLeuGlnThrSerAlaGlnMetGlyTyrValVal 1150                                 1170                                   1190
ATTGATATTGAAGCCGACGAAGACGTTGCCGAAAAAGCCGCTGCAGGCAATGAAAGCTATT
IleAspIleGluAlaAspGluAspValAlaGluLysAlaAlaLeuGlnAlaMetLysAlaIle

FIG. 2-5

```
        1210                              1230
CCGGGTACCATTCGCGCCCGTCTGCTGTACTAA
ProGlyThrIleArgAlaArgLeuLeuTyrEnd
```

MATERIALS AND METHODS FOR BIOSYNTHESIS OF SERINE AND SERINE-RELATED PRODUCTS

CROSS REFERENCE TO RELATED APPLICATION

This patent application is a Continuation-In-Part of U.S. patent application Ser. No. 08/244,491 filed May 24, 1994 which is a 371 of PCT/EP92/01873, filed Aug. 17, 1992, and now U.S. Pat. No. 5,618,716.

BACKGROUND OF THE INVENTION

1. Field of the Invention

This invention relates to the general field of biosynthesis of serine and products related to serine, particularly tryptophan, and to methods and materials used in that biosynthesis.

2. The Prior Art

Serine is a primary intermediate in the biosynthesis of a wide variety of cellular metabolites including such economically important compounds as choline, glycine, cysteine and tryptophan. In addition, serine acts as a single carbon donor and is responsible for 60% to 75% of the total need of the cell for $C_1$ units through the production of 5,10-methylenetetrahydrofolate from tetrahydrofolate. These $C_1$ units are used in a wide variety of biosynthetic pathways including the synthesis of methionine, inosine monophosphate, other purines and some pyrimidines (e.g., thymidine and hydroxymethyl cytidine).

The serine biosynthetic pathway shown in FIG. 1 is generally available to a wide variety of tissues and mirroorganisms. The first committed step in that pathway is the conversion of 3-phospho-D-glyceric acid (PGA) to 3-phosphohydroxypyruvic acid (PHA) by means of the enzyme 3-phosphoglycerate dehydrogenase (PGD). The gene encoding PGD has been cloned and sequenced, and the amino acid sequence of the PGD subunit has been deduced. Tobey and Grant, *J. Biol. Chem.*, 261:12179–12183 (1980).

In procaryotes (particularly bacteria) and microorganisms such as yeast, but not in higher eukaryotes, activity of wild-type PG is inhibited by cellular serine levels. This inhibition has been studied kinetically and reportedly proceeds in an allosteric manner. Tobey and Grant, *J. Biol. Chem.*, 261:12179–12183 (1986); Dubrow and Pizer, *J. Biol. Chem.*, 252:1527–1551 (1977); McKitrick and Pizer, *J. Bacteriol.*, 141:235–245 (1980).

Tosa and Pizer, *J. Bacteriol.*, 106:972–982 (1971), studied the effect of a normally toxic serine analog, L-serine hydroxamate, on an *E. coli* strain. Selection on a growth medium containing that analog yielded analog-resistant mutants. Some mutants were shown to have a modification in an enzyme unrelated to PGD, seryl-tRNA synthetase. Crude extract of one mutant showed PGD activity with reduced serine sensitivity (See, *J. Bacteriol.*, 106:972–982 [1971]; FIG. 5; Table 6; and see p. 973 bottom left col., p. 977 bottom left col.).

SUMMARY OF THE INVENTION

One aspect of the invention generally features DNA encoding 3-phosphoglycerate dehydrogenase (PGD) with reduced sensitivity to inhibition by serine in comparison to wild-type PGD, i.e., the DNA encodes PGD which has at least some level of enzymatic activity useful for biosynthesis, and which retains that activity at higher serine levels than does the (unmodified) wild-type PGD.

In preferred embodiments, the wild-type PGD is microbial or yeast PGD. Also preferably, the engineered DNA encodes PGD which comprises an alteration in the C-terminal 25% of wild-type PGD, preferably in the C-terminal 50 amino acids. For example, the engineered DNA may encode PGD comprising a deletion in part of all of the C-terminus. Also preferably, the engineered DNA encodes PGD having an insertion in the C-terminus (e.g., between VAL 363 and ASN 364, or between ALA 393 and GLN 395) in addition to the deletion described above, or as a separate alteration.

The present invention is also directed to: a) PGD having the amino acid sequence of the above-described engineered DNA; b) expression vectors comprising the engineered DNA and regulatory DNA positioned and oriented for expression of the engineered DNA in a host expression system; c) cells comprising such expression vectors; and d) methods for producing serine or a serine-derived product by culturing such cells. As to c) above, the cell preferably is deleted for wild-type serA.

Yet another embodiment generally features a cell engineered (e.g., it includes a recombinant genetic construction) to produce a PGD-encoding mRNA transcript with an altered 3' end, which transcript is translated by the cell to yield. PGD with reduced sensitivity to inhibition by serine in comparison to wild-type PGD.

The present invention provides decontrol of an important biosynthetic control point, thereby enhancing production of numerous compounds downstream of that point, including, in particular, serine and serine-derived products such as tryptophan. Other cellular metabolites derived from serine (i.e., serine is a primary intermediate in their biosynthesis) include choline, glycine, cysteine and $C_1$-donor-dependent compounds such as methionine, inosine monophosphate, purines, and some pyrimidines (e.g., thymidine and hydroxymethyl cytosine).

BRIEF DESCRIPTION OF THE DRAWINGS

Other objects and features of the present invention will become apparent from the following detailed description considered in connection with the accompanying drawings, which disclose the embodiments of the present invention. It should be understood, however, that the drawings are designed for the purpose of illustration only and not as a definition of the limits of the invention.

In the drawings, wherein similar reference characters denote similar elements throughout the several views:

FIGS. 2(1)–2(5) show the sequence of the *E. coli* serA gene reported by Tobey and Grant (cited above) and the amino acid sequence deduced from the gene.

DETAILED DESCRIPTION OF THE PREFERRED EMBODIMENTS

Providing Serine-Insensitive PGD

Figure 1:
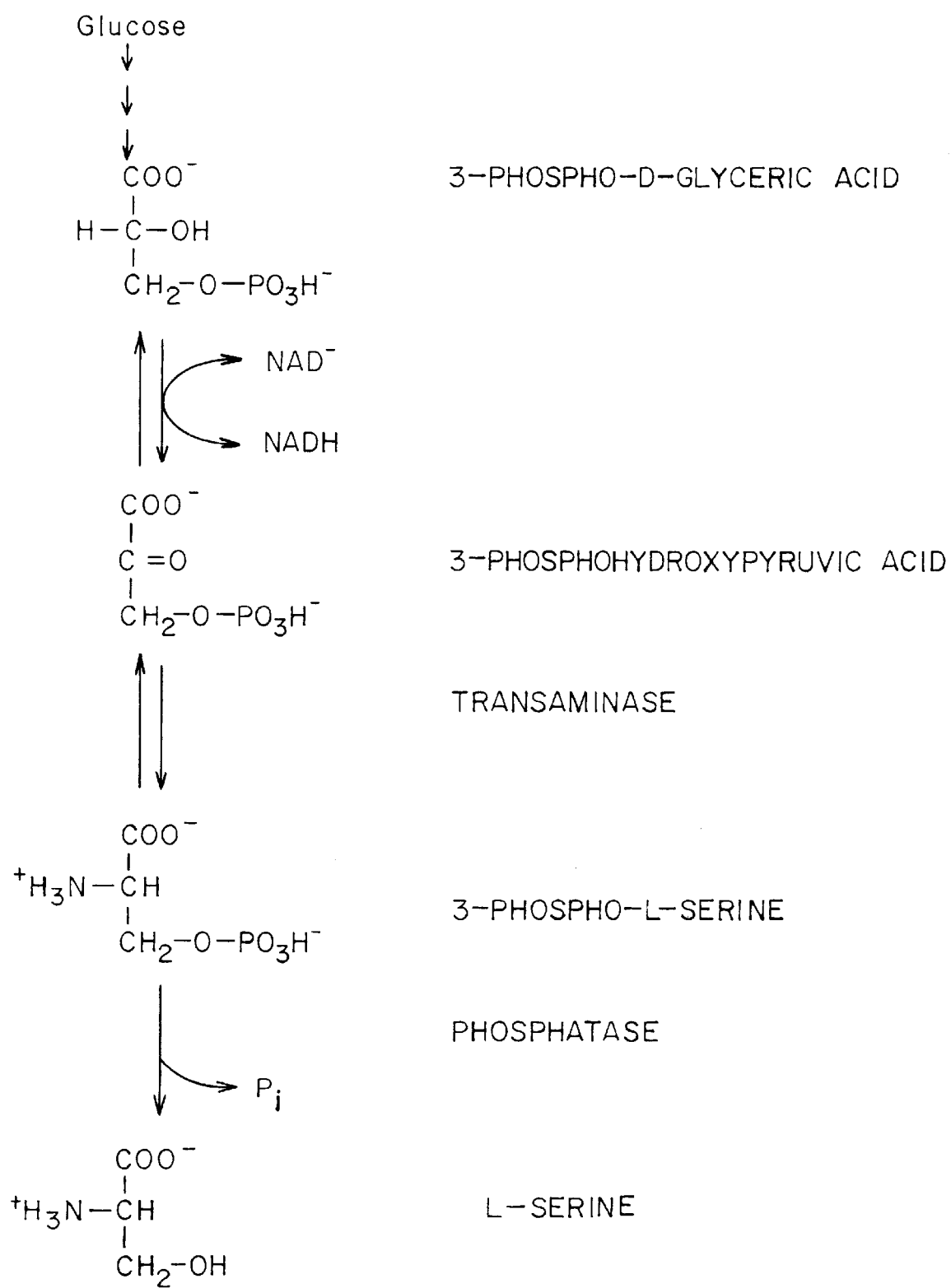
FIG. 1 shows the steps in the biosynthesis of L-serine from glucose.

1. Genetically Engineered Constructions.

The preferred embodiments of the invention feature biosynthesis of serine and serine-related products, e.g., products described above derived by biosynthesis from serine. A first step in biosynthesis of these compounds according to the invention is the provision of serine-insensitive PGD, as discussed below.

It has been determined that there is a specific serine feedback mediating domain in PGD, and that domain can be altered to reduce serine sensitivity while maintaining useful levels of PGD activity. FIG. 2 shows one particular PGD genetic and amino acid sequence (SEQ ID NO: 1) which can be used for reference in the following discussion. The sequence of FIG. 2 (SEQ ID NO: 1) includes 410 amino acids (including the initial Met which is cleaved from the mature protein). The domain of PGD that can reduce serine sensitivity, without destroying PGD activity, is within the C-terminal 25% of the molecule, most preferably the 50 C-terminal residues.

Thus from 42 to 52 C-terminal amino acids may be deleted from the wild-type of PGD of SEQ ID NO:1 and an amino acid sequence can be inserted in place of these deleted C-terminal amino acids.

Examples of PGD modifications that fall within the invention are deletions of some or all of the C-terminal 42 amino acids, or insertions or substitutions within that region which reduce serine insensitivity while retaining useful PGD function. For example, insertion of amino acid residues between Val 363 and Asn 364 will increase the $K_i$ of the PGD over wild-type, while retaining PGD activity.

More dramatic increases in $K_i$ are accomplished by deleting some or all of the C-terminal amino acid residues. For example, deletion of the C-terminal residues GTIRARLLY and replacement with ASLD increases $K_i$ by several orders of magnitude, while retaining a useful level of PGD activity. Other insertions within the scope of the invention are insertions between Ala 393 and Gln 395.

Other useful modifications include deletions from the C-terminus in addition to the insertions and modifications discussed above.

Genes encoding serine-insensitive PGD described above can be constructed by genetic engineering techniques that involve altering the 3' end of the coding region coding for the C-terminal amino acids, and then transforming a host strain with a vehicle to express the altered PGD enzyme. Candidate altered enzymes are screened (as described below) for serine affinity ($K_i$) and for PGD activity by the methods generally discussed below.

2. Screening the Genetically Engineered Constructions.

In screening genetic constructions made by the above-described methods, the following assays of PGD activity and of serine sensitivity are used.

While not critical to the invention, the assay of PGD activity is generally necessary in order to establish the degree of serine sensitivity of the altered enzyme. As is well known in the art, enzyme activity is a function of the total number of enzyme molecules and the catalytic activity of each molecule. Thus, in comparing the catalytic activity of PGD feedback variants, steps must be taken to adequately control for the relative number of PGD molecules for samples in which relative catalytic activity is to be compared. There are a number of ways in which this may be accomplished. However, since it is difficult to adequately establish the level of gene expression in cells transformed with truncated serA genes (due to decreased viability), the most suitable way to compare PGD activity produced from various constructs and the wild type is to chromosomally integrate the altered serA gene containing standard regulatory elements in a single copy, followed by harvesting the transformants and determination of the relative catalytic activity as compared to PGD from wild type cells.

Any method suitable for the measurement of PGD activity may be employed. PGD activity may be measured through detection of either the forward or the reverse reaction by the method of John C. McKitrick and Lewis I. Pizer, *J. Bacteriol.*, 141:235–245 (1980).

The enzymatic assay described above is suitable for determination of serine sensitivity for any PGD enzyme, including those with chemically modified C-termini. The assay is performed in the presence of various levels of serine. The catalytic activity in the presence of serine is compared to catalytic activity in the absence of serine, and the $K_i$ calculated.

In most cases it will be preferred to reduce serine sensitivity without significantly altering PGD catalytic activity. In still other embodiments it may be desirable to reduce both the feedback sensitivity and the catalytic activity. The constructions having a C-terminal amino acid sequence of 3-phosphoglycerate dehydrogenases listed in TABLE 1 and in TABLE 1A (described below) may be used.

TABLE 1

C-terminal Amino Acid Sequences of 3-phosphoglycerate dehydrogenases

| serA | Sequence | Ki/mM | Units |
|---|---|---|---|
| WT | (SEQ ID NO: 2) | 0.02 | 0.05 |
| 1455 | (SEQ ID NO: 3) | >100 | <.01 |
| 1459 | (SEQ ID NO: 4) | >100 | N/A |
| 1507 | (SEQ ID NO: 5) | >100 | N/A |
| 1508 | (SEQ ID NO: 6) | 3.8 | 0.05 |
| 1509 | (SEQ ID NO: 7) | >100 | N/A |
| 1510 | (SEQ ID NO: 8) | >100 | N/A |
| 1511 | (SEQ ID NO: 9) | >100 | N/A |
| 1512 | (SEQ ID NO: 10) | >100 | N/A |
| 1530 | (SEQ ID NO: 11) | >100 | N/A |
| 1531 | (SEQ ID NO: 12) | >100 | N/A |

TABLE 1A

C-Terminal Amino Acid Sequence of wildtype and mutated serA alleles

| serA | Sequence | Ki/mM | Units |
|---|---|---|---|
| WT | (SEQ ID NO: 2) | 0.02 | 0.05 |
| 11 | (SEQ ID NO: 13) | 50 | 0.0375 |
| 5 | (SEQ ID NO: 14) | 0.25 | 0.0375 |
| 4 | (SEQ ID NO: 15) | 0.025 | 0.025 |
| 7 | (SEQ ID NO: 16) | 0.025 | 0.0075 |
| 8 | (SEQ ID NO: 17) | 0.03 | 0.0075 |
| 9 | (SEQ ID NO: 18) | 0.03 | 0.0125 |
| 10 | (SEQ ID NO: 19) | 5 | 0.01 |
| 3/2 | (SEQ ID NO: 20) | 20 | 0.0025 |

Other constructions with modified 3' ends also fall within the scope of the present invention since it is a simple matter to prepare test constructs and transform cells according to the prepare invention and test for serine inhibition of PGD activity.

Any vector which leads to expression of a PGD protein lacking sensitivity to inhibition by serine pertains to the present invention. In general, however, in the absence of a sink for serine, high levels of expression of feedback free PGD should be avoided since the resulting high cytoplasmic levels of serine or serine-derived metabolites can be toxic to the cell. Thus, in general, for any construct coding for a feedback inhibited PGD with normal catalytic activity and expression levels similar to those from the native gene, transformation will likely lead to high levels of PGD expression and decreased cellular viability. The toxicity of high levels of serine produced may, in fact, select for mutants with decreased PGD expression. Thus, while transformation using multi-copy plasmids may be useful in initial screening of constructs with some embodiments, it is preferred to chromosomally integrate serA constructs in single copies into the genome. Additionally, chromosomal integration as described below facilitates activity measurement of the feedback deleted PGD. Thus, in most embodiments where strong catalytic activity is expected or desired, it is preferred to utilize vectors suitable for single copy chromosomal integration. Many such vectors and strategies for their use are known in the art. See, e.g., Backman, U.S. Ser. No. 07/091,837, filed Sep. 1, 1987, hereby incorporated by reference. Useful vectors and constructs can be made to allow for the successful transformation and expression of the enzyme in an appropriate host for producing the desired product. Means for accomplishing these ends are well known to those familiar with the art and are not central to the present invention. In addition to the altered PGD-encoding DNA, the expression vector will contain various other elements described below.

First, the coding sequences present on the vector will be accompanied by the appropriate regulatory elements necessary for the appropriate level of expression of the coding sequences, including promoters, ribosome binding sites, and termination sequences. In most cases, the native serA regulatory sequences will be the preferred source of the catalytically active part of the molecule, although it is recognized that many other regulatory sequences known to the art or yet to be discovered may be employed.

Second, it is preferred that sequences encoding selective markers and/or reporter genes, along with the appropriate regulatory elements, will also be present on the vector. The expression of such selective markers is useful in identifying transformants. Appropriate selective marker genes include those coding for ampicillin, tetracycline, and chloramphenicol.

Third, the desirability of an origin of replication on the plasmid vector depends largely on the desirability of maintaining the genes chromosomally or extrachromosomally. Those familiar with the art appreciate the various strategies by which the lack of an origin of replication can be exploited to promote integration into the chromosome. See, e.g., Backman et al., U.S. Pat. No. 4,743,546, hereby incorporated by reference.

Once the expression vector is constructed, a suitable host cell can be transformed with a vector containing a transcription unit coding for a serine insensitive PGD protein. In most cases, it is useful to employ cells for which the endogenous PGD protein is known to be inhibited by serine and in which the endogenous serA gene is deleted and replaced by the altered gene of the invention. Such cell systems are useful for the overproduction of serine-related metabolites. Cells known to contain serine sensitive proteins are prokaryotes and yeasts.

The following examples illustrate, but do not limit, the invention.

EXAMPLE 1

Construction of serA Gene Alleles Encoding Feedback Resistant 3-phosphoglycerate Dehydrogenases The *E. coli* K12 serA gene was isolated on a 6.4 Kb DNA fragment from a Sau3A partial digest cloned into the BclI site of pTR264. See, Backman et al., U.S. Ser. No. 07/285,128, filed Dec. 16, 1988; and Roberts et al., Gene, 12:123 (1980). This plasmid was named pKB1302. A 3 Kb SalI to SphI fragment of pKB1302 DNA containing the serA gene was cloned into pUC19 to generated pKB1321. pKB1370 was generated by cloning a 3 Kb HindIII to SalI fragment containing the serA gene into pBR322.

Alleles of serA encoding feedback resistant 3-phosphoglycerate dehydrogenases were generated by inserting XbaI linkers at restriction sites in the 3' region of the serA gene. A partial digest of plasmid pKB1321 by HincII yielded blunt ends at position 1793, where insertion of linkers gave: a) pKB1459, encoding a truncated 3-phosphoglycerate dehydrogenase; b) pKB1507, encoding a truncated 3-phosphoglycerate dehydrogenase; and c) pKB1508 which encodes a 3-phosphoglycerate dehydrogenase with a four amino acid residue insert.

PstI digestion of pKB 1321 gives 3' overhang at position 1888. Blunt ends were generated by the action of the Klenow fragment of DNA polymerase I. Linkers were ligated into the blunt end fragments and the derived plasmids were pKB1509 which encodes a 3-phosphoglycerate dehydrogenase with a two-amino-acid insert and pKBp510 which encodes a truncated 3-phosphoglycerate dehydrogenase. A KpnI digest of pKB1370 was made blunt ended with Klenow fragment of DNA polymerase I and inserted linkers yielded plasmids encoding truncated 3-phosphoglycerate dehydrogenase, pKB1455 and pKB1512, or 3-phosphoglycerate dehydrogenase with a two amino acid residue insert, pKB1511. Deletion plasmids pKB1530 and pKB1531 were generated by inserting the 0.8 Kb BamHI to XbaI fragment from pKB1508 or the 0.9 Kb BamHI to XbaI fragment from pKB1509, respectively, into the 5.8 Kb BamHI to XbaI fragment of pKB1511.

The following TABLE 2 summarizes the various constructs made.

TABLE 2

| serA Allele | Plasmid | Restriction Site | Linker | Result |
| --- | --- | --- | --- | --- |
| Ser A 1455 | pKB 1370 | Kpn I | SEQ ID NO: 21 | Truncated |
| Ser A 1459 | pKB 1321 | Hind II | SEQ ID NO: 21 | Truncated |
| Ser A 1507 | pKB 1321 | Hind II | SEQ ID NO: 22 | Truncated |
| Ser A 1508 | pKB 1321 | Hind II | SEQ ID NO: 23 | Insert |
| Ser A 1509 | pKB 1321 | Pst I | SEQ ID NO: 24 | Insert |
| Ser A 1510 | pKB 1321 | Pst I | SEQ ID NO: 23 | Truncated |
| Ser A 1511 | pKB 1370 | Kpn I | SEQ ID NO: 25 | Insert |
| Ser A 1512 | pKB 1370 | Kpn I | SEQ ID NO: 26 | Truncated |
| Ser A 1530 | pKB 1511 + pKB 1508 | Hind II + Kpn I | | Deleted |
| Ser A 1531 | pKB 1511 + pKB 1509 | Pst I + Kpn I | | Deleted |

For all the constructs, the starting vector, the restriction site used, and the sequence of the inserted linker are indicated. The Ki values for serine are given in Table 1, as well as the relative catalytic activity for three of these constructs following chromosomal integration (described below). N/A indicates that the construction was not chromosomally integrated, and the activity level therefore was not standardized.

3. Chemical Modifications

Those skilled in the art will understand that deletions or modifications of the C-terminus of wild-type PGD can be accomplished enzymatically or chemically, e.g., by various carboxypeptidases, including carboxypeptidase Y or by lactoperoxidase mediated iodination.

4. Use of Antisense mRNA

Alternatively, it may be possible to reduce serine sensitivity in vivo through the generation of PGD-encoding transcripts truncated at the 3' end by means of the producing antisense mRNAs that include nucleotide sequences complementary to portions of the 3' coding region of native or transformed PGD coding sequences.

C. Production of Desired Compounds

Figure 3:
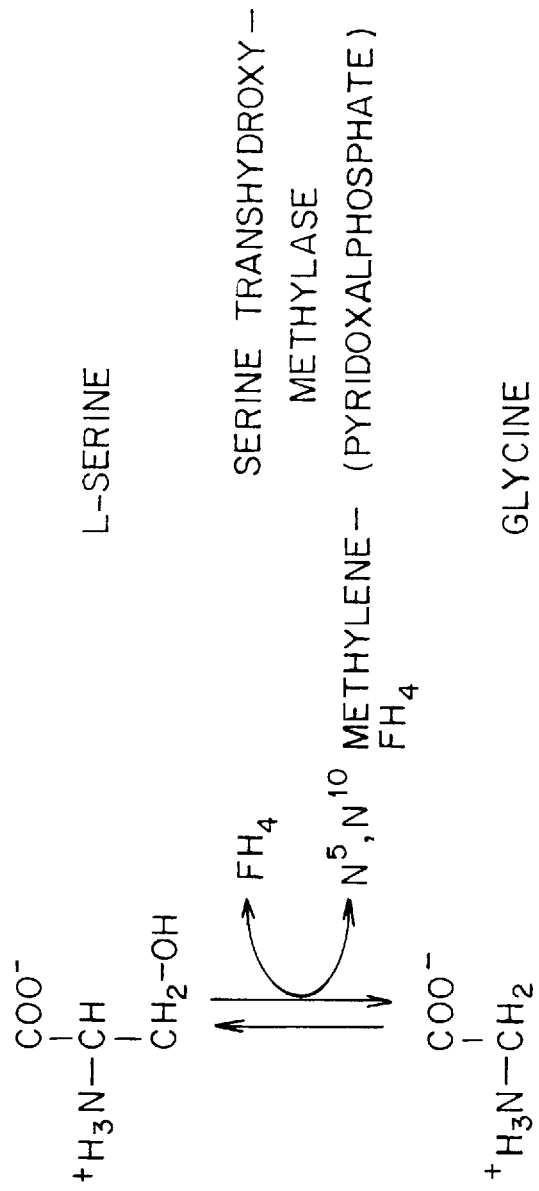
FIG. 3 depicts bioconversion of L-serine and tetrahydrofolate to glycine and $N^5$, $N^{10}$-methylene tetrahydrofolate.

As shown in FIG. 3, serine is an intermediate in the production of glycine. It is also an intermediate in the production of $N^5,N^{10}$-methylenetetrahydrofolate, which is generalized $C_1$ donor essential for synthesis of methionine, purines (including inosine) and some pyrimidines. Thus, the over-production of serine from phosphoglycerate may be useful in a wide range of bacterial production systems, including production systems for choline, glycine, cysteine, methionine, tryptophan, and purines, including inosine monophosphate.

The following specific examples further illustrate the invention.

EXAMPLE 2

Host Strain Preparation

Sequences internal to a plasmid born serA gene were replaced with a kanamycin resistance gene. This plasmid was then used to inactivate the host strain serA gene by means of allele exchange, as follows.

The serA region of YMC9 (ATCC33920) was cloned from chromosomal DNA, partially digested with Sau 3AI, by complementation of PC1523 (argI61, argF58, serA27, purA54, thr-25, tonA49, relA1, spoT1), obtained from Coli Genetic Stock Center, Yale University, New Haven, Conn. A 3 kb fragment carrying the serA gene was subcloned into pUC19, giving rise to a plasmid called pKB13-21. From this plasmid, a 3 kb SalI to HindIII fragment was recloned into pBR322, giving rise to plasmid pKB1370. The KpnI site at the 3' end of the serA gene was converted to BamHI with a linker and the BamHI fragment internal to the resulting serA was replaced with the BamHI fragment from pUC-4-KSAC (Pharmacia) containing the Tn903 kanamycin resistance gene. This new plasmid was designated pKB1429. A pBR322 derivative called pKB 701 (ATCC39772) (see U.S. Ser. No. 06/757,014, hereby incorporated by reference) was generated in which the MboI and TThIII 1 flanking the origin of replication were converted to KpnI sites. The SalI to EcoRI fragment containing serA::KanR from pKB1429 was cloned into pKB701, giving rise to pKB1438. pKB1438 was digested with KpnI to remove the ori region. The large fragment containing the ampicillin resistance coding region, as well as the serA::KanR, was circularized and used in a $CaCl_2$ transformation of YMC9. Following transformation, the host YMC9 cells were placed under selection on ampicillin. Under these conditions, ampicillin resistant clones develop by incorporation of the circular DNA through homologous recombination in the serA gene flanking regions. Growth of the ampicillin resistant isolate in the absence of ampicillin selection results in loss of the ampicillin resistance gene by homologous recombination of the repeated sequences of serA gene flanking regions. Such strains were identified by the loss of production of β-lactamase using AmpScreen (BRL) according to the manufacturer's directions. Duplicate streaking of single colonies on media in the presence and absence of serine revealed ampicillin sensitive clones requiring serine for growth on minimal medium and which were also resistant to kanamycin. One such isolate was named KB875.

EXAMPLE 3

Chromosomal Integration of Altered serA Sequences by Allele Exchange

The serA 1455 allele was introduced to the chromosome by a process analogous to that used for the introduction of serA::KanR as described in Example 2. Briefly, a fragment (SalI to HindIII) bearing the serA 1455 allele was cloned into pKB701. The plasmid origin was removed by KpnI digestion. The circularized DNA was used to transform to ampicillin resistance.

After non-selective growth, using Ampscreen and replica plating for kanamycin, KB904 (serA 1455) was isolated and shown to be sensitive to ampicillin and kanamycin. The resulting serA 1455 allele can be transferred into production strains by P1 transduction. Miller, *Experiments in Mol. Genetics*, Cold Spring Harbor Press, pp. 201–205 (1972).

EXAMPLE 4

Chromosomal Integration of Altered serA Sequences by recD Dependent Gene Replacement Another approach was utilized to move the serA1508 allele on to the chromosome. The strain KB875 was made recD by P1 transduction from V220 (recD, argA:Tn10. Amundsen et al., *Proc. Acad. Sci., U.S.A.*, 82:5558–5562 [1986]) (DSM 6823). The gene for an essential third subunit of exonuclease V. to give JGP101. The plasmid pKB1508 was linearized and used to transform JGP101 to serine prototrophy essentially as described by Shevell et al., *J. Bacteriol.*, 170:3294–3296 (1988), to give JGP103. The serA1508 allele can then be moved to production strains by P1 transduction. Miller et al., *Experiments in Mol. Genetics*, Cold Spring Harbor Lab., pp. 201–205 (1972).

Harvesting of Overproduced Metabolites

For the overproduction of serine-related metabolites, cells can be prepared which produce PGD with reduced serine sensitivity, and grown in fermentors under the appropriate conditions, in most cases to stationary phase. The cells will then be harvested and lysed and the desired metabolite prepared according to standard biochemical procedures. Conditions, principles, and references for the growth of microbes, and the harvesting of specific metabolites, are provided by Crueger and Crueger, *Biotechnology: A Textbook of Industrial Biology* (1982) and Herrmann and Somerville, *Amino Acids: Biosynthesis and Genetic Regulation* (1983), incorporated herein by reference.

While several embodiments of the present invention have been shown and described, it is to be understood that many changes and modifications may be made thereunto without departing from the spirit and scope of the invention as defined in the appended claims.

What is claimed is:

1. Engineered DNA encoding 3-phosphoglycerate dehydrogenase (PGD) from *E. Coli* with reduced sensitivity to inhibition by serine in comparison to wild-type PGD;
    said DNA encoding PGD from *E. Coli* in which from 42 to 52 C-terminal amino acids have been deleted from the wild-type PGD of (SEQ ID NO:1) and in which an amino acid sequence has been inserted in place of the deleted C-terminal amino acids.

2. The engineered DNA of claim 1, in which said DNA encodes PGD having an amino acid sequence in which the 52 C-terminal amino acids have been deleted and in which an amino acid sequence selected from the group consisting of
    (SEQ ID NO.: 13);
    (SEQ ID NO.: 14);
    (SEQ ID NO.: 15);
    (SEQ ID NO.: 16);
    (SEQ ID NO.: 17);
    (SEQ ID NO.: 18);
    (SEQ ID NO.: 19); and
    (SEQ ID NO.: 20);
has been inserted instead of the deleted 52 C-terminal amino acids of the wild-type PGD of (SEQ ID NO:1).

3. A 3-phosphoglycerate dehydrogenase having the amino acid sequence encoded by the engineered DNA of claim 1.

4. An expression vector comprising
    the engineered DNA of claim 1 and regulatory DNA positioned and oriented for expressing said engineered DNA in a host expression system.

5. A cell comprising the engineered DNA of claim 1, and regulatory DNA positioned and oriented to express said engineered DNA in said cell.

6. The cell of claim 5, in which said cell is deleted for wild-type serA.

7. A method for producing a product selected from the group consisting of serine and a serine-derived product, comprising culturing a cell according to claim 5; and
  recovering said product.

8. The method of claim 7, in which said product is serine.

9. The engineered DNA of claim 1,
  wherein 42 C-terminal amino acids have been deleted from the wild-type PGD of (SEQ ID NO:1).

10. The engineered DNA of claim 1,
  wherein 50 C-terminal amino acids have been deleted from the wild-type PGD of (SEQ ID NO:1).

11. The engineered DNA of claim 1,
  wherein 52 C-terminal amino acids have been deleted from the wild-type PGD of (SEQ ID NO:1).

* * * * *

SEQUENCE LISTING ( 1 ) GENERAL INFORMATION:

( i i i ) NUMBER OF SEQUENCES: 26

( 2 ) INFORMATION FOR SEQ ID NO:1:

( i ) SEQUENCE CHARACTERISTICS:
( A ) LENGTH: 1233 base pairs
( B ) TYPE: nucleic acid
( C ) STRANDEDNESS: double
( D ) TOPOLOGY: linear ( i i ) MOLECULE TYPE: other DNA ( x i ) SEQUENCE DESCRIPTION: SEQ ID NO:1:

```
ATG  GCA  AAG  GTA  TCG  CTG  GAG  AAA  GAC  AAG  ATT  AAG  TTT  CTG  CTG  GTA      48
Met  Ala  Lys  Val  Ser  Leu  Glu  Lys  Asp  Lys  Ile  Lys  Phe  Leu  Leu  Val
 1              5                        10                       15

GAA  GGC  GTG  CAC  CAA  AAG  GCG  CTG  GAA  AGC  CTT  CGT  GCA  GCT  GGT  TAC      96
Glu  Gly  Val  His  Gln  Lys  Ala  Leu  Glu  Ser  Leu  Arg  Ala  Ala  Gly  Tyr
             20                       25                       30

ACC  AAC  ATC  GAA  TTT  CAC  AAA  GGC  GCG  CTG  GAT  GAT  GAA  CAA  TTA  AAA     144
Thr  Asn  Ile  Glu  Phe  His  Lys  Gly  Ala  Leu  Asp  Asp  Glu  Gln  Leu  Lys
         35                       40                       45

GAA  TCC  ATC  CGC  GAT  GCC  CAC  TTC  ATC  GGC  CTG  CGA  TCC  CGT  ACC  CAT     192
Glu  Ser  Ile  Arg  Asp  Ala  His  Phe  Ile  Gly  Leu  Arg  Ser  Arg  Thr  His
     50                       55                       60

CTG  ACT  GAA  GAC  GTG  ATC  AAC  GCC  GCA  GAA  AAA  CTG  GTC  GCT  ATT  GGC     240
Leu  Thr  Glu  Asp  Val  Ile  Asn  Ala  Ala  Glu  Lys  Leu  Val  Ala  Ile  Gly
 65                       70                       75                       80

TGT  TTC  TGT  ATC  GGA  ACA  AAC  CAG  GTT  GAT  CTG  GAT  GCG  GCG  GCA  AAG     288
Cys  Phe  Cys  Ile  Gly  Thr  Asn  Gln  Val  Asp  Leu  Asp  Ala  Ala  Ala  Lys
                      85                       90                       95

CGC  GGG  ATC  CCG  GTA  TTT  AAC  GCA  CCG  TTC  TCA  AAT  ACG  CGC  TCT  GTT     336
Arg  Gly  Ile  Pro  Val  Phe  Asn  Ala  Pro  Phe  Ser  Asn  Thr  Arg  Ser  Val
                 100                      105                      110

GCG  GAG  CTG  GTG  ATT  GGC  GAA  CTG  CTG  CTG  CTA  TTG  CGC  GGC  GTG  CCG     384
Ala  Glu  Leu  Val  Ile  Gly  Glu  Leu  Leu  Leu  Leu  Leu  Arg  Gly  Val  Pro
             115                      120                      125

GAA  GCC  AAT  GCT  AAA  GCG  CAC  CGT  GGC  GTG  TGG  AAC  AAA  CTG  GCG  GCG     432
Glu  Ala  Asn  Ala  Lys  Ala  His  Arg  Gly  Val  Trp  Asn  Lys  Leu  Ala  Ala
         130                      135                      140

GGT  TCT  TTT  GAA  GCG  CGC  GGC  AAA  AAG  CTG  GGT  ATC  ATC  GGC  TAC  GGT     480
Gly  Ser  Phe  Glu  Ala  Arg  Gly  Lys  Lys  Leu  Gly  Ile  Ile  Gly  Tyr  Gly
145                      150                      155                      160

CAT  ATT  GGT  ACG  CAA  TTG  GGC  ATT  CTG  GCT  GAA  TCG  CTG  GGA  ATG  TAT     528
His  Ile  Gly  Thr  Gln  Leu  Gly  Ile  Leu  Ala  Glu  Ser  Leu  Gly  Met  Tyr
                      165                      170                      175

GTT  TAC  TTT  TAT  GAT  ATT  GAA  AAT  AAA  CTG  CCG  CTG  GGC  AAC  GCC  ACT     576
Val  Tyr  Phe  Tyr  Asp  Ile  Glu  Asn  Lys  Leu  Pro  Leu  Gly  Asn  Ala  Thr
                 180                      185                      190

CAG  GTA  CAG  CAT  CTT  TCT  GAC  CTG  CTG  AAT  ATG  AGC  GAT  GTG  GTG  AGT     624
Gln  Val  Gln  His  Leu  Ser  Asp  Leu  Leu  Asn  Met  Ser  Asp  Val  Val  Ser
             195                      200                      205

CTG  CAT  GTA  CCA  GAG  AAT  CCG  TCC  ACC  AAA  AAT  ATG  ATG  GGC  GCG  AAA     672
Leu  His  Val  Pro  Glu  Asn  Pro  Ser  Thr  Lys  Asn  Met  Met  Gly  Ala  Lys
         210                      215                      220

GAA  ATT  TCA  CTA  ATG  AAG  CCC  GGC  TCG  CTG  CTG  ATT  AAT  GCT  TCG  CGC     720
Glu  Ile  Ser  Leu  Met  Lys  Pro  Gly  Ser  Leu  Leu  Ile  Asn  Ala  Ser  Arg
225                      230                      235                      240
```

| | | | | | | | | | | | | | | | | |
|---|---|---|---|---|---|---|---|---|---|---|---|---|---|---|---|---|
| GGT | ACT | GTG | GTG | GAT | ATT | CCG | GCG | CTG | TGT | GAT | GCG | CTG | GCG | AGC | AAA | 768 |
| Gly | Thr | Val | Val | Asp | Ile | Pro | Ala | Leu | Cys | Asp | Ala | Leu | Ala | Ser | Lys | |
| | | | | 245 | | | | | 250 | | | | | 255 | | |
| CAT | CTG | GCG | GGG | GCG | GCA | ATC | GAC | GTA | TTC | CCG | ACG | GAA | CCG | GCG | ACC | 816 |
| His | Leu | Ala | Gly | Ala | Ala | Ile | Asp | Val | Phe | Pro | Thr | Glu | Pro | Ala | Thr | |
| | | | 260 | | | | | 265 | | | | | 270 | | | |
| AAT | AGC | GAT | CCA | TTT | ACC | TCT | CCG | CTG | TGT | GAA | TTC | GAC | AAC | GTC | CTT | 864 |
| Asn | Ser | Asp | Pro | Phe | Thr | Ser | Pro | Leu | Cys | Glu | Phe | Asp | Asn | Val | Leu | |
| | | 275 | | | | | 280 | | | | | 285 | | | | |
| CTG | ACG | CCA | CAC | ATT | GGC | GGT | TCG | ACT | CAG | GAA | GCG | CAG | GAG | AAT | ATC | 912 |
| Leu | Thr | Pro | His | Ile | Gly | Gly | Ser | Thr | Gln | Glu | Ala | Gln | Glu | Asn | Ile | |
| | 290 | | | | | 295 | | | | | 300 | | | | | |
| GGC | CTG | GAA | GTT | GCG | GGT | AAA | TTG | ATC | AAG | TAT | TCT | GAC | AAT | GGC | TCA | 960 |
| Gly | Leu | Glu | Val | Ala | Gly | Lys | Leu | Ile | Lys | Tyr | Ser | Asp | Asn | Gly | Ser | |
| 305 | | | | | 310 | | | | | 315 | | | | | 320 | |
| ACG | CTC | TCT | GCG | GTG | AAC | TTC | CCG | GAA | GTC | TCG | CTG | CCA | CTG | CAC | GGT | 1008 |
| Thr | Leu | Ser | Ala | Val | Asn | Phe | Pro | Glu | Val | Ser | Leu | Pro | Leu | His | Gly | |
| | | | | 325 | | | | | 330 | | | | | 335 | | |
| GGG | CGT | CGT | CTG | ATG | CAC | ATC | CAC | GAA | AAC | CGT | CCG | GGC | GTG | CTA | ACT | 1056 |
| Gly | Arg | Arg | Leu | Met | His | Ile | His | Glu | Asn | Arg | Pro | Gly | Val | Leu | Thr | |
| | | | 340 | | | | | 345 | | | | | 350 | | | |
| GCG | CTG | AAC | AAA | ATC | TTC | GCC | GAG | CAG | GGC | GTC | AAC | ATC | GCC | GCG | CAA | 1104 |
| Ala | Leu | Asn | Lys | Ile | Phe | Ala | Glu | Gln | Gly | Val | Asn | Ile | Ala | Ala | Gln | |
| | | 355 | | | | | 360 | | | | | 365 | | | | |
| TAT | CTG | CAA | ACT | TCC | GCC | CAG | ATG | GGT | TAT | GTG | GTT | ATT | GAT | ATT | GAA | 1152 |
| Tyr | Leu | Gln | Thr | Ser | Ala | Gln | Met | Gly | Tyr | Val | Val | Ile | Asp | Ile | Glu | |
| | 370 | | | | | 375 | | | | | 380 | | | | | |
| GCC | GAC | GAA | GAC | GTT | GCC | GAA | AAA | GCG | CTG | CAG | GCA | ATG | AAA | GCT | ATT | 1200 |
| Ala | Asp | Glu | Asp | Val | Ala | Glu | Lys | Ala | Leu | Gln | Ala | Met | Lys | Ala | Ile | |
| 385 | | | | | 390 | | | | | 395 | | | | | 400 | |
| CCG | GGT | ACC | ATT | CGC | GCC | CGT | CTG | CTG | TAC | TAA | | | | | | 1233 |
| Pro | Gly | Thr | Ile | Arg | Ala | Arg | Leu | Leu | Tyr | End | | | | | | |
| | | | | 405 | | | | | 410 | | | | | | | |

(2) INFORMATION FOR SEQ ID NO:2:

(i) SEQUENCE CHARACTERISTICS:
        (A) LENGTH: 52 amino acids
        (B) TYPE: amino acid
        (D) TOPOLOGY: linear (ii) MOLECULE TYPE: peptide (xi) SEQUENCE DESCRIPTION: SEQ ID NO:2:

| | | | | | | | | | | | | | | |
|---|---|---|---|---|---|---|---|---|---|---|---|---|---|---|
| Ala | Glu | Gln | Gly | Val | Asn | Ile | Ala | Ala | Gln | Tyr | Leu | Gln | Thr | Ser | Ala |
| 1 | | | | 5 | | | | | 10 | | | | | 15 | |
| Gln | Met | Gly | Tyr | Val | Val | Ile | Asp | Ile | Glu | Ala | Asp | Glu | Asp | Val | Ala |
| | | | 20 | | | | 25 | | | | | 30 | | | |
| Glu | Lys | Ala | Leu | Gln | Ala | Met | Lys | Ala | Ile | Pro | Gly | Thr | Ile | Arg | Ala |
| | | 35 | | | | 40 | | | | | 45 | | | | |
| Arg | Leu | Leu | Tyr | | | | | | | | | | | | |
| | 50 | | | | | | | | | | | | | | |

(2) INFORMATION FOR SEQ ID NO:3:

(i) SEQUENCE CHARACTERISTICS:
        (A) LENGTH: 47 amino acids
        (B) TYPE: amino acid
        (D) TOPOLOGY: linear (ii) MOLECULE TYPE: peptide (xi) SEQUENCE DESCRIPTION: SEQ ID NO:3:

```
Ala  Glu  Gln  Gly  Val  Asn  Ile  Ala  Ala  Gln  Tyr  Leu  Gln  Thr  Ser  Ala
 1              5                        10                            15

Gln  Met  Gly  Tyr  Val  Val  Ile  Asp  Ile  Glu  Ala  Asp  Glu  Asp  Val  Ala
               20                       25                  30

Glu  Lys  Ala  Leu  Gln  Ala  Met  Lys  Ala  Ile  Pro  Ala  Ser  Leu  Asp
          35                       40                       45
```

( 2 ) INFORMATION FOR SEQ ID NO:4:

( i ) SEQUENCE CHARACTERISTICS:
        ( A ) LENGTH: 7 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:4:

```
Ala  Glu  Gln  Gly  Val  Leu  Val
 1              5
```

( 2 ) INFORMATION FOR SEQ ID NO:5:

( i ) SEQUENCE CHARACTERISTICS:
        ( A ) LENGTH: 6 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:5:

```
Ala  Glu  Gln  Gly  Val  Leu
 1              5
```

( 2 ) INFORMATION FOR SEQ ID NO:6:

( i ) SEQUENCE CHARACTERISTICS:
        ( A ) LENGTH: 56 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:6:

```
Ala  Glu  Gln  Gly  Val  Cys  Ser  Arg  Ala  Asn  Ile  Ala  Ala  Gln  Tyr  Leu
 1              5                        10                            15

Gln  Thr  Ser  Ala  Gln  Met  Gly  Tyr  Val  Val  Ile  Asp  Ile  Glu  Ala  Asp
               20                       25                  30

Glu  Asp  Val  Ala  Glu  Lys  Ala  Leu  Gln  Ala  Met  Lys  Ala  Ile  Pro  Gly
          35                       40                       45

Thr  Ile  Arg  Ala  Arg  Leu  Leu  Tyr
          50                  55
```

( 2 ) INFORMATION FOR SEQ ID NO:7:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:7:

```
Ala  Glu  Gln  Gly  Val  Asn  Ile  Ala  Ala  Gln  Tyr  Leu  Gln  Thr  Ser  Ala
 1              5                        10                            15

Gln  Met  Gly  Tyr  Val  Val  Ile  Asp  Ile  Glu  Ala  Asp  Glu  Asp  Val  Ala
               20                       25                  30
```

Glu Lys Ala Leu Ser Arg Gln Ala Met Lys Ala Ile Pro Gly Thr Ile
          35                      40                      45

Arg Ala Arg Leu Leu Tyr
          50

( 2 ) INFORMATION FOR SEQ ID NO:8:

( i ) SEQUENCE CHARACTERISTICS:
        ( A ) LENGTH: 37 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:8:

Ala Glu Gln Gly Val Asn Ile Ala Ala Gln Tyr Leu Gln Thr Ser Ala
 1                   5                      10                      15

Gln Met Gly Tyr Val Val Ile Asp Ile Glu Ala Asp Glu Asp Val Ala
              20                      25                      30

Glu Lys Ala Leu Leu
          35

( 2 ) INFORMATION FOR SEQ ID NO:9:

( i ) SEQUENCE CHARACTERISTICS:
        ( A ) LENGTH: 54 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:9:

Ala Glu Gln Gly Val Asn Ile Ala Ala Gln Tyr Leu Gln Thr Ser Ala
 1                   5                      10                      15

Gln Met Gly Tyr Val Val Ile Asp Ile Glu Ala Asp Glu Asp Val Ala
              20                      25                      30

Glu Lys Ala Leu Gln Ala Met Lys Ala Ile Pro Gly Ser Arg Ala Ile
          35                      40                      45

Arg Ala Arg Leu Leu Tyr
          50

( 2 ) INFORMATION FOR SEQ ID NO:10:

( i ) SEQUENCE CHARACTERISTICS:
        ( A ) LENGTH: 45 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:10:

Ala Glu Gln Gly Val Asn Ile Ala Ala Gln Tyr Leu Gln Thr Ser Ala
 1                   5                      10                      15

Gln Met Gly Tyr Val Val Ile Asp Ile Glu Ala Asp Glu Asp Val Ala
              20                      25                      30

Glu Lys Ala Leu Gln Ala Met Lys Ala Ile Pro Val Leu
          35                      40                      45

( 2 ) INFORMATION FOR SEQ ID NO:11:

( i ) SEQUENCE CHARACTERISTICS:
        ( A ) LENGTH: 16 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:11:

Ala Glu Gln Gly Val Cys Ser Arg Ala Ile Arg Ala Arg Leu Leu Tyr
1               5                   1 0                  1 5

( 2 ) INFORMATION FOR SEQ ID NO:12:

( i ) SEQUENCE CHARACTERISTICS:
        ( A ) LENGTH: 46 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:12:

Ala Glu Gln Gly Val Asn Ile Ala Ala Gln Tyr Leu Gln Thr Ser Ala
1               5                   1 0                  1 5

Gln Met Gly Tyr Val Val Ile Asp Ile Glu Ala Asp Glu Asp Val Ala
                2 0              2 5                  3 0

Glu Lys Ala Leu Ser Arg Ala Ile Arg Ala Arg Leu Leu Tyr
            3 5              4 0                  4 5

( 2 ) INFORMATION FOR SEQ ID NO:13:

( i ) SEQUENCE CHARACTERISTICS:
        ( A ) LENGTH: 55 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:13:

Ala Glu Gln Gly Val Cys Ser Arg Ala Asn Ile Ala Ala Gln Tyr Leu
1               5                   1 0                  1 5

Gln Thr Ser Ala Gln Met Gly Tyr Val Val Ile Asp Ile Glu Ala Asp
                2 0              2 5                  3 0

Glu Asp Val Ala Glu Lys Ala Leu Gln Ala Met Lys Ala Ile Pro Gly
            3 5              4 0                  4 5

Thr Ile Arg Ala Arg Leu Leu
    5 0              5 5

( 2 ) INFORMATION FOR SEQ ID NO:14:

( i ) SEQUENCE CHARACTERISTICS:
        ( A ) LENGTH: 51 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:14:

Ala Glu Gln Gly Val Asn Ile Ala Ala Gln Tyr Leu Gln Thr Ser Ala
1               5                   1 0                  1 5

Gln Met Gly Tyr Val Val Ile Asp Ile Glu Ala Asp Glu Asp Val Ala
                2 0              2 5                  3 0

Glu Lys Ala Leu Gln Ala Met Lys Ala Ile Pro Gly Thr Ile Arg Ala
            3 5              4 0                  4 5

Arg Leu Leu
    5 0

( 2 ) INFORMATION FOR SEQ ID NO:15:

( i ) SEQUENCE CHARACTERISTICS:
    ( A ) LENGTH: 50 amino acids
    ( B ) TYPE: amino acid
    ( D ) TOPOLOGY: linear ( i i ) MOLECULE TYPE: peptide ( x i ) SEQUENCE DESCRIPTION: SEQ ID NO:15:

Ala Glu Gln Gly Val Asn Ile Ala Ala Gln Tyr Leu Gln Thr Ser Ala
 1               5                   10                  15

Gln Met Gly Tyr Val Val Ile Asp Ile Glu Ala Asp Glu Asp Val Ala
            20                  25                  30

Glu Lys Ala Leu Gln Ala Met Lys Ala Ile Pro Gly Thr Ile Arg Ala
         35                  40                  45

Arg Leu
     50

( 2 ) INFORMATION FOR SEQ ID NO:16:

( i ) SEQUENCE CHARACTERISTICS:
        ( A ) LENGTH: 49 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:16:

Ala Glu Gln Gly Val Asn Ile Ala Ala Gln Tyr Leu Gln Thr Ser Ala
 1               5                   10                  15

Gln Met Gly Tyr Val Val Ile Asp Ile Glu Ala Asp Glu Asp Val Ala
            20                  25                  30

Glu Lys Ala Leu Gln Ala Met Lys Ala Ile Pro Gly Thr Ile Arg Ala
         35                  40                  45

Arg ( 2 ) INFORMATION FOR SEQ ID NO:17:

( i ) SEQUENCE CHARACTERISTICS:
        ( A ) LENGTH: 48 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:17:

Ala Glu Gln Gly Val Asn Ile Ala Ala Gln Tyr Leu Gln Thr Ser Ala
 1               5                   10                  15

Gln Met Gly Tyr Val Val Ile Asp Ile Glu Ala Asp Glu Asp Val Ala
            20                  25                  30

Glu Lys Ala Leu Gln Ala Met Lys Ala Ile Pro Gly Thr Ile Arg Ala
         35                  40                  45

( 2 ) INFORMATION FOR SEQ ID NO:18:

( i ) SEQUENCE CHARACTERISTICS:
        ( A ) LENGTH: 47 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:18:

Ala Glu Gln Gly Val Asn Ile Ala Ala Gln Tyr Leu Gln Thr Ser Ala
 1               5                   10                  15

Gln Met Gly Tyr Val Val Ile Asp Ile Glu Ala Asp Glu Asp Val Ala
            20                  25                  30

Glu Lys Ala Leu Gln Ala Met Lys Ala Ile Pro Gly Thr Ile Arg
            35                  40                  45

( 2 ) INFORMATION FOR SEQ ID NO:19:

( i ) SEQUENCE CHARACTERISTICS:
        ( A ) LENGTH: 46 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:19:

Ala Glu Gln Gly Val Asn Ile Ala Ala Gln Tyr Leu Gln Thr Ser Ala
 1               5                  10                  15

Gln Met Gly Tyr Val Val Ile Asp Ile Glu Ala Asp Glu Asp Val Ala
            20                  25                  30

Glu Lys Ala Leu Gln Ala Met Lys Ala Ile Pro Gly Thr Ile
            35                  40                  45

( 2 ) INFORMATION FOR SEQ ID NO:20:

( i ) SEQUENCE CHARACTERISTICS:
        ( A ) LENGTH: 45 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:20:

Ala Glu Gln Gly Val Asn Ile Ala Ala Gln Tyr Leu Gln Thr Ser Ala
 1               5                  10                  15

Gln Met Gly Tyr Val Val Ile Asp Ile Glu Ala Asp Glu Asp Val Ala
            20                  25                  30

Glu Lys Ala Leu Gln Ala Met Lys Ala Ile Pro Gly Thr
            35                  40                  45

( 2 ) INFORMATION FOR SEQ ID NO:21:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:21:

CTAGTCTAGA CTAG                                                            1 4

( 2 ) INFORMATION FOR SEQ ID NO:22:

( i ) SEQUENCE CHARACTERISTICS:
        ( A ) LENGTH: 8 base pairs
        ( B ) TYPE: neucleic acid
        ( C ) STRANDEDNESS: double
        ( D ) TOPOLOGY: linear ( i i ) MOLECULE TYPE: DNA ( x i ) SEQUENCE DESCRIPTION: SEQ ID NO:22:

CTCTAGAG                                                                8

( 2 ) INFORMATION FOR SEQ ID NO:23:

(i) SEQUENCE CHARACTERISTICS:
    (A) LENGTH: 12 base pairs
    (B) TYPE: nucleic acid
    (C) STRANDEDNESS: double
    (D) TOPOLOGY: linear (ii) MOLECULE TYPE: DNA (xi) SEQUENCE DESCRIPTION: SEQ ID NO:23:

TGCTCTAGAG CA                                                                            12

(2) INFORMATION FOR SEQ ID NO:24:

(i) SEQUENCE CHARACTERISTICS:
    (A) LENGTH: 10 base pairs
    (B) TYPE: nucleic acid
    (C) STRANDEDNESS: double
    (D) TOPOLOGY: linear (ii) MOLECULE TYPE: DNA (xi) SEQUENCE DESCRIPTION: SEQ ID NO:24:

GCTCTAGAGC                                                                               10

(2) INFORMATION FOR SEQ ID NO:25:

(i) SEQUENCE CHARACTERISTICS:
    (A) LENGTH: 10 base pairs
    (B) TYPE: nucleic acid
    (C) STRANDEDNESS: double
    (D) TOPOLOGY: linear (ii) MOLECULE TYPE: DNA (xi) SEQUENCE DESCRIPTION: SEQ ID NO:25:

GCTCTAGAGC                                                                               10

(2) INFORMATION FOR SEQ ID NO:26:

(i) SEQUENCE CHARACTERISTICS:
    (A) LENGTH: 11 base pairs
    (B) TYPE: nucleic acid
    (C) STRANDEDNESS: double
    (D) TOPOLOGY: linear (ii) MOLECULE TYPE: DNA (xi) SEQUENCE DESCRIPTION: SEQ ID NO:26:

TGCTCTAGAG C                                                                             11